United States Patent [19]

Székely

[11] 3,968,130
[45] July 6, 1976

[54] PROCESS FOR THE NITRATION OF ANTHRAQUINONES

[75] Inventor: Istvan Székely, Basel, Switzerland

[73] Assignee: Ciba-Geigy AG, Basel, Switzerland

[22] Filed: Oct. 25, 1972

[21] Appl. No.: 300,689

[30] Foreign Application Priority Data
Oct. 26, 1971 Switzerland.................. 15542/71
Mar. 16, 1972 Switzerland................... 3938/72

[52] U.S. Cl.............................. 260/369; 260/383; 260/384
[51] Int. Cl.²........................................ C07C 79/37
[58] Field of Search................. 260/369, 383, 384

[56] References Cited
UNITED STATES PATENTS

| | | | |
|---|---|---|---|
| 2,302,729 | 11/1942 | Whelen............................ | 260/369 |
| 2,874,168 | 2/1959 | Graham et al................... | 260/369 |
| 3,798,243 | 3/1974 | Toth............................... | 260/369 |

OTHER PUBLICATIONS
Beisler et al., J.A.C.S. 44 pp. 2298–2303 (1944).
Reichel et al., as cited in CA. 70, 38877z (1969).

*Primary Examiner*—Jane S. Myers
*Attorney, Agent, or Firm*—Joseph G. Kolodny; Edward McC. Roberts; Prabodh I. Almaula

[57] ABSTRACT

The invention relates to a process for the manufacture of anthraquinones which are mononitrated in the α-position, especially 1-nitroanthraquinone, wherein an anthraquinone which possesses at least 1 free α-position and is optionally substituted in the other α-position with halogen, preferably chlorine, or with hydroxyl groups, but especially the unsubstituted anthraquinone, is nitrated with concentrated nitric acid without further additives adiabatically, or at temperature above 40°C isothermically, and optionally under pressure.

2 Claims, No Drawings

PROCESS FOR THE NITRATION OF ANTHRAQUINONES

The present invention provides a new process for the nitration of anthraquinones by means of which it is possible to obtain on an industrial scale pure products which are nitrated in the α-position, for example 1-nitroanthraquinone, 1-chloro-4-nitroanthraquinone, 1,5-dichloro-4-nitroanthraquinone.

The nitration of anthraquinones which possess at least 1 free α-position and in the other α-positions are optionally substituted by halogen, preferably by chlorine or by hydroxyl groups, has been carried out as a rule hitherto in a mixture of sulphuric acid and nitric acid, in the process of which product mixtures were obtained, the separation of which in most cases was not feasible technically (see S. Coffey, Chemistry and Industry) 1953, page 1070).

Besides the method with sulphuric and nitric acid, further methods for nitrating the unsubstituted anthraquinone have been cited, according to which the process is carried out in other solvents and the nitration of the anthraquinone is meant to proceed selectively to give the 1-nitroanthraquinone. According to Polish Patent Application No. 46248 of 31.7.1961, it is supposed to be possible to manufacture pure 1-nitroanthraquinone by nitrating the anthraquinone with potassium nitrate in hydrofluoric acid at 60°C under pressure. On putting this latter process to the test experimentally, however, instead of the pure 1-nitroanthraquinone it was only possible to obtain a mixture which, in its composition according to analysis by gas chromatography, corresponded to those mixtures which are obtainable by nitration in sulphuric acid; in addition to 20 % unchanged anthraquinone, it was possible to detect 7 % 2-anthraquinone and 18 % dinitroanthraquinone derivatives.

Also, according to the process protected in U.S. Pat. No. 2,874,168, the nitration in concentrated nitric acid is intended to proceed selectively respecting the 1-nitroanthraquinone, i.e. for all practical purposes only this product is to be formed, the condition being that the temperature is kept at 25°C and may on no account exceed 40°C. The reaction time is said to be between 12 to 100 hours. Verification of those particulars, and of the Examples provided, also proved that unchanged anthraquinone and dinitroanthraquinones as well as 2-nitroanthraquinone together constitute 15–20 % of the resulting mixture, and that these impurities are precipitated together with the 1-nitroanthraquinone when using the cited working up method. In no way can the product be described as pure 1-nitroanthraquinone. Besides the very lenghty reaction times necessary (up to 100 hours), the process of U.S. Pat. No. 2,874,168 therefore also has the disadvantage that no purification is attained by the working up method. It is, of course, possible to separate the 1-nitroanthraquinone from non-reacted anthraquinone and from the 2-nitro derivatives by the known method of reprecipitation from sulphuric acid, but the particulary troublesome dinitroanthraquinones cannot be removed, so that a qualitatively unusuable mixture of aminoanthraquinones results in the reduction. In contradistinction to the particulars of the cited U.S. patent the surprising discovery has now been made that, on the one hand, the selectivity of the nitration of the anthraquinone in concentrated nitric acid is scarcely influenced by changes in temperature, so that even at temperatures of over 40°C mixtures are obtained which in their composition are the equal of the mixtures obtainable at 25°C and correspondingly longer reaction time and, on the other hand, that the desired 1-nitroanthraquinone crystallises selectively at low temperatures from the reaction mixtures present following the nitration, preferably at a temperature of at least −20°C, in the process of which the dianthraquinones and the 2-nitroanthraquinone remain for the most part in solution. Accordingly, it is possible to separate 1-nitroanthraquinone from 2-nitro-anthraquinone and from dinitroanthraquinones by crystallisation from concentrated nitric acid at low temperature.

The finding that the selectivity of the nitration is not dependent on temperatures is of dual importance for the development of an industrial process: on the one hand, the reaction time is shortened at higher temperatures so that the process becomes more economic, and on the other hand, it is possible to carry out the process adiabatically, it being necessary neither to cool nor to warm the reaction mixture.

The discovery has also been made that it is possible to manufacture nitration mixtures in analogous manner by treating anthraquinones, which are substituted with halogen, particuarly chlorine, or with hydroxyl groups, with concentrated nitric acid without the addition of sulphuric acid, and from which mixtures the mononitro derivative can be isolated in the indicated manner. According to this last named process, it is possible to obtain, for example, mononitro derivatives of 1-chloroanthraquinone, and 1,5-dichloro-anthraquinone.

The invention therefore relates to a process for the manufacture and isolation of anthraquinones which are nitrated in the α-position, wherein an anthraquinone which possesses at least 1 free α-position and is optionally substituted in the other α-position with halogen, preferably chlorine, or with hydroxyl groups, is nitrated with concentrated nitric acid without further additives adiabatically, or at temperatures above 40°C isothermically, and optionally under pressure. If it is necessary to isolate dinitroanthraquinones from the reaction mixtures, it is advantageous to proceed in such a manner that the α-mononitroanthraquinone is precipitated by cooling the mixture of nitroanthraquinones dissolved in concentrated nitric acid and isolated from the mother liquor which contains the β-nitroanthraquinone and/or dinotroanthraquinones. In the adiabatic process, the temperature of the mixture increases through its own heat of reaction. The rise in temperature is a criterion for the degree of nitration. (The average number of nitro groups per anthraquinone molecule present in the mixture multiplied with a factor 100 gives the degree of nitration in percent). Depending on the concentration ratios the reaction solution may heat to above boiling point, so that the process must be carried out under pressure. Since the amounts of energy which become liberated during the nitration are known, it is possible to calculate in advance at what temperature the desired degree of nitration is reached. Of course, the reaction can also be carried out isothermically instead of adiabatically, i.e. in this case with cooling, in the process of which the heat liberated can be measured via a heat detector. Instead of controlling the liberated heat of reaction, it is also possible to follow the reaction by measuring other physical values, such as conductivity, specific weight, potential etc. The composition of the reaction mixture can be inferred from the degree of nitration.

The detailed procedure to be followed for the nitration of the anthraquinone is that the anthraquinone is treated with concentrated nitric acid either adiabatically in a temperature range from about 30°C up to boiling point optionally under pressure or isothermically at 40°C to 70°C, preferably at 45°C. If the reaction is discontinued at a degree of nitration of over 80 %, preferably at 90 to 110 %, the mixture contains substantial amounts of dinitroanthraquinone. The working up is carried out in this case preferably by cooling the nitration mixture at −10°C to −40°C, preferably −20°C to −25°C, when the 1-nitroanthraquinone crystallises out and the dinitroanthraquinones and the 2-nitroanthraquinone remain virtually completely in solution. The nitration solution must be cooled to 10°–20°C rapidly in order that the reaction proceeds no further. This is advantageously done by mixing it with super-cooled recirculating reaction solution. The further cooling to about −20°C may follow slowly. In a laboratory test it is often more economical to stop the reaction by pouring the solution on ice, filtering off the precipitated product and dissolving it again at room temperature in concentrated nitric acid.

An alternative method of obtaining 1-nitroanthraquinones consists in discontinuing the reaction when a 55 % to 80 % degree of nitration is reached. This is readily possible in the inventive process of adiabatic nitration in concentrated nitric acid, since the degree of nitriation can be observed from the change in temperature of the reaction mixture. In this case only about 1–5 % of dinitroanthraquinone is formed, so that instead of the low temperature crystallisation from concentrated nitric acid, the following known method of processing can be utilised: the nitration mixture is poured on ice or, after cooling by mixing it with recirculating reaction solution, diluted with water and the precipitated product filtered off. The mixture of nitrated anthraquinones is then treated with sodium sulphite, in the process of which the 2-nitroanthraquinone is converted selectively into water-soluble derivatives. After filtration, a mixture of 1-nitroanthraquinone and anthraquinone remains as insoluble product. This is reduced and subsequently consists of 1-aminoanthraquinone and anthraquinone. The aminoanthraquinone is dissolved by treating it with sulphuric acid (e.g. 60 %). The residual insoluble anthraquinone is used again as starting product for the nitration.

For the nitration and subsequent crystallisation process, it is advantageous to use about 6 to 100, preferably 10 to 20, moles of nitric acid to 1 mole of anthraquinone. Surprisingly, it has been found that the concentration ratios influence the selectivity of the nitration in such a way that an improved selectivity respecting the moninitration is achieved on using a substantial excess of nitric acid. The nitric acid should have a concentration of 85 % to 100 %.

A particularly high degree of purity is achieved in the case of the nitration of the unsubstituted anthraquinone by combining the new crystallisation process with the already known reprecipitation from sulphuric acid. In this way 1-nitroanthraquinone, which is free from anthraquinone, dinitroanthraquinone and 2-nitroanthraquinone, is obtained.

In industrial production it is advantageous to carry out the nitration continuously, using conventional apparatus such as cascades or pipe reactors. The reaction course can also be controlled in this case with the aid of parameters, such as specific weight, conductivity and, especially, temperature and enthalpy change. The working up is performed by rapidly cooling the reaction mixture, preferably by mixing it with recirculating, supercooled reaction solution.

The mother liquor which occurs according to the process and in the case of the nitration of the unsubstituted anthraquinone consists principally of dinitroanthraquinone, nonreacted anthraquinone and 2-nitroanthraquinone, can be further processed according to the process of the invention, so that it is possible to avoid waste products.

The process to be followed in this connection is that the mother liquor is heated again after filtering off the 1-nitroanthraquinone which has crystallised on cooling, and the nitration is continued until only dinitroanthraquinones are still present in the mixture. These can be isolated by, for example, pouring the reaction solution on ice. The resulting mixture of dinitroanthraquinone is a valuable industrial intermediate.

After isolation of the nitrated products and of the unchanged anthraquinone, a 40°–50°C nitric acid remains as mother liquor. Optionally after distillation, this liquor can be processed to highly concentrated nitric acid or it may be used for the manufacture of artificial fertilisers (ammonium nitrate).

The advantage of the new process is that nitration mixtures of favourable composition can be manufactured in simple manner. In particular, conditions for the nitration of anthraquinones have been found which require only a relatively short reaction time, so that a continuous mode of operation for this process becomes possible. Due to the high reaction temperatures which are possible according to the invention, the reaction can be carried out without cooling, i.e. adiabatically. This form of operation is distinguished by a particularly simple method of controlling the reaction course; it is sufficient to follow the temperature of the nitration mixture. In addition, the process according to the invention affords the opportunity of dispensing with the anthraquinone-1-sulphonic acid used as starting material in the existing method of producing 1-aminoanthraquinone. For environmental reasons this is most desirable, since mercury deposits result in its manufacture.

The new purification process — crystallisation of the product from concentrated nitric acid, optionally directly from the nitric acid used as reaction medium — additionally gives rise to a technically feasible way of isolating the dinitro derivatives from the desired mononitroanthraquinone. In the case of the nitration of anthraquinone, a process has been discovered which permits the industrial manufacture of 1-nitroanthraquinone in great purity by combining this method of purification with the known reprecipitation from sulphuric acid.

The products obtained according to the invention have a varied use as intermediates, in particular as starting products for α-aminoanthraquinones which are of importance in the manufacture of dyestuffs.

The following Examples illustrate the invention, the parts and percentages being by weight unless otherwise states.

EXAMPLE 1

677.2 parts of 96.4 % nitric acid are preheated to 53°C, then 189 parts of anthraquinone are added thereto within 2 minutes, in the course of which all the constituents pass into solution immediately while being stirred vigorously. In the process thereof, the temperature rises to 56°C.

The temperature of the reaction mixture is subsequently kept at 55°C. A sample taken after 2 hours shows the following composition:

| | |
|---|---|
| 1-nitroanthraquinone | 68.7 % |
| anthraquinone | 3.0 % |
| 2-nitroanthraquinone | 9.1 % |
| dinitroanthraquinone | 19.2 % |

This composition corresponds in every respect to the composition of those samples which result from nitrations carried out at lower temperatures but after substantially longer reaction times.

The solution is then cooled to −22°C. The resulting crystalline product is filtered off at this temperature and then stirred with water. The crystals are filtered off with suction, the filter product is washed with water until the washings run neutral, and dried. The product is subsequently reprecipitated from sulphuric acid to give practically pure, i.e. 98 %, 1-nitroanthraquinone.

EXAMPLE 2

525 parts of 96.4 % nitric acid are cooled to 15°C. While stirring vigorously, 156 parts of anthraquinone are added to the nitric acid, whereupon immediately everything passes into solution. The solution is kept for 72 hours at 25°C. An analysis shows that, after this time, the solution contains an anthraquinone mixture which consists of 2,5 % anthraquinone, 68 % 1-nitroanthraquinone, 9,4 % 2-nitroanthraquinone, and 20.1 % dinitroanthraquinone.

The solution is cooled to −20°C to −22°C. The crystallised product which has fallen out is isolated by filtration and washed with 150 parts of 92 % nitric acid which has a temperature of −25°C. The crystallised product is stirred with water, the crystals are then filtered with suction and washed with water until the washings run neutral. The resulting product contains 85.4 % of 1-nitroanthraquinone, 3.1 % of anthraquinone, 5.2 % of 2-nitroanthraquinone, and 6.3 % of dinitroanthraquinone. The crystallisation process is repeated frm 92 % nitric acid and the product is reprecipitated subsequently from sulphuric acid, whereupon 1-nitroanthraquinone is isolated which is 98 % pure.

EXAMPLE 3

314 parts of anthraquinone are dissolved in 1130 parts of 96.4 % nitric acid which has a temperature of 25°C, and the solution is kept for 49 hours at this temperature. An analysis shows that it contains a mixture of anthraquinones consisting of 73 % 1-nitroanthraquinone, 7.9 % anthraquinone, 8 % 2-nitroanthraquinone, and 11.1 % dinitroanthraquinone. The solution is cooled to −22°C. The resulting crystallised product is isolated at this temperature and stirred with water. The crystals are filtered with suction, washed with water until the washings run neutral, and dried, to give 213 parts of a product which consists of 86.5 % 1-nitroanthraquinone, 8.3 % anthraquinone and only 1.9 % 2-nitroanthraquinone as well as 3.3 % dinitroanthraquinone. This mixture is reprecipitated from sulphuric acid to give pure (98 %) 1-nitroanthraquinone.

EXAMPLE 4

1100 parts of 98 % nitric acid are heated to 35°C in a flask having a water equivalent of 300 g. While stirring thoroughly, 208 parts of anthraquinone are added to the acid within 20 seconds, whereupon a homogeneous solution is formed. Neither cooling nor heating is effected (adiabatic method of operation). The mixture warms uniformly and after 90 seconds attains the pre-calculated temperature of 73°C.

The solution is poured on ice within a few seconds, whereupon the reaction product precipitates in crystalline form. The product is filtered with suction, washed with water until the washings run neutral, and dried, to give 253.4 parts of a product which, after analysis by gas chromatography, has the following composition:

| | |
|---|---|
| 1-nitroanthraquinone | 78.2 % |
| anthraquinone | 10.7 % |
| 2-nitroanthraquinone | 4.2 % |
| dinitroanthraquinone | 6.9 % |

The product is dissolved in 92 % nitric acid at room temperature and purified by crystallisation and reprecipitation from sulphuric acid as described in Examples 1 to 3, to give 180 g of pure 1-nitroanthraquinone. Pure 1-amino-anthraquinone is obtained after the reduction.

EXAMPLE 5

100 parts of 99 % nitric acid are preheated to 35°C in a flask having a water equivalent of 300 g. While stirring thoroughly, 208 parts of pure anthraquinone are added within 3 seconds, whereupon practically everything passes into solution immediately. The temperature rises uniformly and reaches 70°C after 90 seconds, whereupon the batch is poured on ice within 12 seconds. The precipitated crystalline nitroanthraquinone is filtered with suction and washed with water until the washings run neutral and dried in vacuo. The product weighs 253 g and after analysis by gas chromotagraphy shows the following composition:

| | |
|---|---|
| 1-nitroanthraquinone | 78.2 % |
| 2-nitroanthraquinone | 4.2 % |
| anthraquinone | 10.7 % |
| dinitroanthraquinone | 6.9 % |

The product is purified by crystallisation from concentrated nitric acid as described in Examples 1 to 4 and yields a qualitatively pure 1-nitroanthraquinone.

EXAMPLE 6

900 parts of 98 % nitric acid are put into a flask having a water equivalent of 200 g. While stirring, 208 parts of pure anthraquinone are added all at once at 35°C. The temperature rises immediately and everything dissolves within a few seconds. The mixture is rapidly poured on 1200 parts of ice at 62.5°C and the anthraquinone mixture is worked up as described in Example 5. The crude product consisting of 53 % 1-nitroanthraquinone, 39 % anthraquinone, 7 % 2-nitroanthraquinone and 1 % dinitroanthraquinone is subsequently isolated from the 2-nitroanthraquinone by the known treatment with sodium sulphite. The residue is reduced in the usual manner with sodium sulphide. The resulting mixture is stirred in 60 % sulphuric acid at 100°C. Under these conditions no anthraquinone dissolves, but all aminoathraquinone present does. By means of filtration the aminoanthraquinones alone passes into the mother liquor can be obtained therefrom by dilution and cooling.

EXAMPLE 7 a. Degree of nitration = 54.2 %

1200 parts of crushed ice are charged into a 3 liter beaker. 900 parts of 98 % nitric acid are put into a reaction vessel and, while stirring, heated within a few minutes to 34°–36°C. Within 5 seconds, 208 parts of 100 % ground anthraquinone as 99.3 % product (=209.5 parts) are charged into the ready prepared, stirred nitric acid. During the immediate exothermic nitration of the anthraquinone over 90 % of the anthraquinone dissolves within 10 seconds (after 1 minute everything has dissolved). With the onset of nitration the solution runs reddish brown and becomes warm. This warming indicates the extent to which the reaction has progressed. As soon as the temperature of the reaction mixture has reached 59°C the stirrer is stopped and as soon as it has reached 62.5°C, the already somewhat bubbling contents of the flask are decanted on the ready prepared ice in the beaker, in the course of which nitrous gases escape. The contents of the beaker are stirred and the resulting pale yellow nitroanthraquinone suspension is then filtered on a porcelain filter (no cotton wool or cellulose fibres!). The filter product is washed with deionised water until neutral and dried in vacuo at 60°C to constant weight. The yield is 232.0 parts of mixture which, according to analysis by gas chromatography, consists of 41.5 % anthraquinone, 51.6 % 1-nitroanthraquinone, 5.8 % 2-nitroanthraquinone and 1.1 % dinitroanthraauinone.

The yield of pure 1-nitroanthraquinone, calculated on the anthraquinone used, is 43.7 % of theory; calculated on the converted anthraquinone it is 88.0 % of theory.

b. Degree of nitration = 65.1 %

The batch is worked up as described in (a), but the reaction mixture is not decanted on ice until the temperature is 67.5°C. The yield is 236.0 parts of a mixture which, according to analysis by gas chromatography, consists of 32.2 % anthraquinone, 57.0 % 1-nitroanthraquinone, 7.7 % 2-nitroanthraquinone and 3.0 % dinitroanthraquinone.

The yield of 1-nitroanthraquinone, calculated on the anthraquinone used, is 53.1 % of theory; calculated on the converted anthraquinone it is 84.2 % of theory.

c. Degree of nitration = 79.0 %

Analogous to variant (a), the following amounts of substance are prepared in the case of this batch; 208 parts of anthraquinone, 1102 parts of nitric acid (98 %), and 1600 parts of ice.

The reaction is performed as described in Example 7 (a), but the stirrer is stopped only when the temperature has reached 62°C and the mixture is not decanted on ice until the final temperature is 67.5°C.

The yields is 245.0 parts of a mixture which; according to analysis by gas chromatography, consists of 20.8 % anthraquinone, 65.0 % 1-nitroanthraquinone, 8.7 % 2-nitroanthraquinone, and 5.4 % dinitroanthraquinone.

The yield of 1-nitroanthraquinone, calculated on the anthraquinone used, is 62.1 % of theory; calculated on converted anthraquinone it is 81.9 % of theory.

I claim:

1. A process for the manufacture of anthraquinone which is mono-nitrated in α-position, wherein anthraquinone is nitrated with concentrated nitric acid, and wherein there are used 6 to 100 moles of nitric acid to 1 mole of anthraquinone, and wherein the nitration is carried out isothermically at a temperature of 40°C to 70°C.

2. A process for the manufacture of anthraquinone which is mono-nitrated in α-position, wherein anthraquinone is nitrated with concentrated nitric acid and wherein there are used 6 to 100 moles of nitric acid to 1 mole of anthraquinone, and wherein the nitration is carried out isothermically at a temperature of 45°C.

* * * * *